United States Patent [19]

Fritzberg et al.

[11] Patent Number: 4,670,545

[45] Date of Patent: Jun. 2, 1987

[54] CHELATING AGENTS FOR TECHNETIUM-99M

[75] Inventors: Alan R. Fritzberg; Sudhakar Kasina, both of Salt Lake City, Utah

[73] Assignee: University Patents, Inc., Westport, Conn.

[21] Appl. No.: 891,044

[22] Filed: Jul. 30, 1986

Related U.S. Application Data

[63] Continuation of Ser. No. 609,172, May 11, 1984, abandoned.

[51] Int. Cl.$^4$ .............................................. C07F 11/00
[52] U.S. Cl. ..................................................... 534/14
[58] Field of Search ....................... 534/14; 260/429 R

[56] References Cited

U.S. PATENT DOCUMENTS

| | | | |
|---|---|---|---|
| 3,803,138 | 4/1974 | Bore .............................. | 260/429 R X |
| 3,873,680 | 3/1975 | Jackson et al. ............. | 260/429 R X |
| 3,928,552 | 12/1975 | Winchell et al. ............ | 260/429 R X |
| 4,054,645 | 10/1977 | Hill et al. ..................... | 260/429 R X |
| 4,057,615 | 11/1977 | Bardy et al. ................. | 260/429 R X |
| 4,434,151 | 2/1984 | Byrne et al. ................. | 260/429 J X |
| 4,444,690 | 4/1984 | Fritzberg ...................... | 260/429 J |

OTHER PUBLICATIONS

Fritzberg et al., J. Nucl. Med. 22, 258–263 (1981).
Davison et al., J. Nucl. Med. 22, pp. 57–58 (1981).
Davison et al., Inorg. Chem. 20(6), pp. 1629–1632 (1981).

*Primary Examiner*—Helen M. S. Sneed
*Attorney, Agent, or Firm*—George M. Yahwak

[57] ABSTRACT

The present invention relates to a novel family of Technetium chelating agents (ligands) based upon amide and mercaptide donor groups.

3 Claims, No Drawings

CHELATING AGENTS FOR TECHNETIUM-99M

Partial funding for the invention described herein came from the U.S. Department of Energy under grant number DE-AC02-83ER60140. In view of this funding, the U.S. government retains certain rights to this invention in accordance with the provisions of 35 USC 202.

This is a continuation of application Ser. No. 609,172, filed May 11, 1984, now abandoned.

1,2-bis (mercaptoacetamido) ethane (commonly referred to as DADS) is a tetradentate chelating agent which has been evaluated as a technetium-99m renal function radiopharmaceutical. (See A. R. Fritzberg et al, *J. Nucl. Med.* 22: 258–263, 1981). Biological studies have indicated that this agent is cleared by the kidneys significantly faster than Tc-99m diethylenetriaminepentaacetic acid (Tc-99m DTPA, $p<0.01$) and slightly slower than I-131 o-iodohippurate ($p>0.05$), with no evidence of significant renal retention. While this agent has shown promise as an imaging agent for the renal system there is need for such agents with higher extraction efficiency and specificity.

Previous research on the synthesis of $N_2S_2$ ligands has resulted in Technetium-99m complexes with superior potential. Technetium-99m-N,N'-bis (mercaptoacetamido)-2,3-diaminopropanoate (Tc-99m $CO_2$-DADS) disclosed in U.S. Pat. No. 4,444,690, the disclosure of which is incorporated in toto, showed higher renal handling efficiency and specificity for one isomer, Tc-99m-$CO_2$DADS-A, that is the first eluting peak on reversed phase octadecylsilyl high-performance liquid chromatography (HPLC). The second isomer (Tc-99m-$CO_2$DADS-B), however, was inferior as reported in the *Journal of Nuclear Medicine* (volume 25, pages 42–48, 1984). Efforts to prepare the complex with only the "A" isomer were unsuccessful. Mixtures of the two epimers resulting from different preparation conditions were never sufficiently high in the "A" isomer to obviate the need for HPLC purification, and, therefore, the Technetium-99m-$CO_2$DADS ligand was deemed to be commercially unfeasible.

Ideally, it is preferred that renal function be evaluated with a single radiopharmaceutical which possesses both high extraction efficiency, such as found with I-131 o-iodohippurate (OIH), and is labeled with a radionuclide having good physical properties such as found with Technetium-99m. Currently, two agents are commonly used in the evaluation of renal function, OIH and Tc-99m DTPA. Renal perfusion is evaluated by rapid serial imaging during the first circulation after bolus injection of Tc-99m DTPA. Normally, OIH cannot be used for the evaluation of renal perfusion because the iodine-131 label limits the amount of radioactivity that can be injected. Renal clearance can be conveniently evaluated with utilizing either Tc-99m DTPA or OIH, however, since Tc-99m DTPA is limited to clearance by glomerular filtration, the maximum approachable extraction efficiency is 20%; secretion of OIH by the renal tubular cells, in addition to some filtration, results in an extraction efficiency approaching 67%. The higher extraction efficiency of OIH increases the kidney-to-background image ratio, and thus increases the sensitivity of OIH for detection and evaluation of reduced renal function.

There is need, therefore, to provide radiopharmaceuticals or radiolabelled contrast agents for the evaluation of renal function which do not contain the detrimental levels of radioactivity found in radioactive iodine, and yet which exhibit a high specificity for renal tubular excretion which is equal to or greater than renal excretion levels obtained when using iodine-131 labelled o-iodohippurate. The ligands of the present invention may be used to form Technetium chelates to serve such needs.

The compounds of the present invention, accordingly, belong to a novel family of chelating agents (ligands) for Technetium. More particularly, this invention relates to the ligands for Technetium-99m which are of the general structural formula:

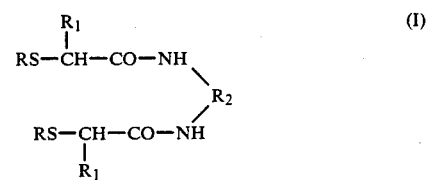

wherein R is selected from the group consisting of —H, —$CH_3$, —$COCH_3$, —$COC_6H_5$, and —$CH_2$NH-$COCH_3$; wherein $R_1$ is selected from the group consisting of —H, —$CH_2CH_3$ and —COOH; wherein $R_2$ is selected from the group consisting of —$CH_2$—$CH_2$—, and —$CH_2$-CHR'—CHR"—; wherein R' and R" are selected from the group consisting of —H, —COOH, and —OH with the proviso that R' and R" are not concurrently —H. Each R substituent may be the same or may be different, and each $R_1$ substituent may be the same or may be different. Depending upon the pH in aqueous solution, certain of these liquids may be salts with alkali metal, for example sodium, or ammonium ions as the cationic moiety of the salt. The present invention also relates to ligands of the compounds of the general formula (I) with radioactive technetium, the method of producing such chelates, and the method of producing ligands of the general formula (I).

Those compounds of the present invention wherein $R_2$ is ethylene, that is wherein $R_2$ is —$CH_2CH_2$—, may be made according to a protocol, modified according to the desired end product ligand, which follows the general overall protocol for the manufacture of the ligand, 1,8-dithiol-2,7-dioxo-3,6-diazanonanoate of formula II. This ligand is also referred to as N-(mercaptoacetyl)-N'-(2-mercapto-3-oxopropanoate) -1,2-diaminoethane, or αS-$CO_2$DADS.

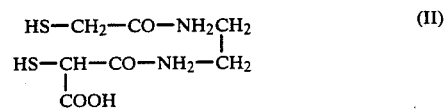

In general, the ligand of formula II is manufactured by a series of steps depicted below:

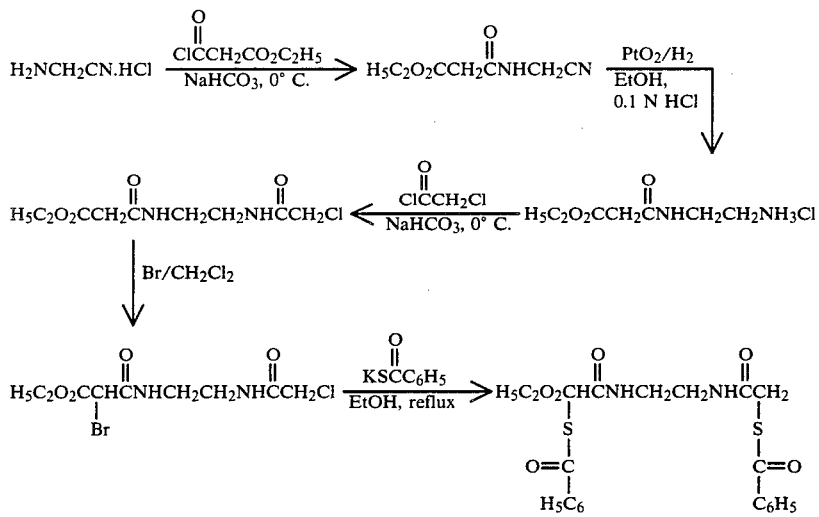

Briefly, this synthesis begins with aminoacetonitrile being acylated with ethyl malonylchloride to yield ethyl N-cyanomethylmalonamide which is then hydrogenated to provide the aminoethyl derivative. This aminoethyl derivative is then acylated with chloroacetyl chloride to the chloroacetamido derivative. Bromine is then introduced at the active methylene position of the malonyl portion of the derivative, and both halides are subsequently displaced with thiobenzoate to the protected sulfhydryl derivative of the ligand as the ethyl ester. By hydrolysis, the ethyl ester and thiol esters are converted to the ligand of formula II. The specific preparation of this ligand may be found in the following Example 1, and the preparation of the Tc-99m complex of this ligand and Technetium may be found in the following Example 2.

EXAMPLE 1

αS-CO₂DADS

Aminoacetonitrile hydrochloride (5.0 g, 0.054 mol) was dissolved in 300 ml of toluene. After cooling in an ice bath, 300 ml of saturated NAHCO₃ was added with stirring. Ethyl malonylchloride (15.0 g, 0.10 mol) dissolved in 50 ml of toluene was added dropwise with rapid stirring. During the addition, dry NaHCO₃ was occasionally added. After the addition, the reaction mixture was allowed to come to room temperature and stirring continued for 15 hrs. Layers were separated and the aqueous phase extracted several times with AcOEt. The extracts were combined with the toluene phase, washed with water, brine, and dried (Na₂SO₄). Removal of solvent left 8.80 g (96%) of product which was used without purification.

Ethyl N-cyanomethylmalonamide (4.0 g, 0.024 mol) was dissolved in 50 ml of absolute EtOH. To the solution was added 2.5 ml of conc. HCl. After purging with N₂ for 10 min 0.40 g of Adam's catalyst was added. The mixture was purged for another 10 min with N₂ and then hydrogenated at 50 psi for 12 hrs. After filtration the solvent was removed to give 4.80 g (97%) of crude product.

The product ethyl N-(2-aminoethyl)malonamide hydrochloride (5.0 g, 0.024 mol) was dissolved in 200 ml of toluene. After cooling in an ice bath 200 ml of saturated NaHC₃ was added. While rapidly stirring 15.0 g (0.133 mol) of chloroacetyl chloride in 50 ml of toluene was added dropwise over a 1 hr period. The reaction mixture was allowed to come to room temperature and stirring was continued for 15 hrs. The layers were separated and the aqueous layer was extracted with AcOEt. The extracts and toluene layer were combined, dried (Na₂SO₄), and solvent removed to give 4.30 g (72%) of white solid product that was used without purification.

Ethyl N-(2-chloroacetamidoethyl) malonamide (1.50 g, 0.0060 mol) was dissolved in 100 ml of CHCl₃. While stirring, a solution of 1.0 g (0.0060 mol) of Br₂ in 15 ml of CHCl₃ was added. After 10 mins. the reaction mixture color changed to pale yellow. After 30 mins., the solution was washed with water, dried (Na₂SO₄), and solvent removed. The solid residue contained a mixture of mono and dibromo products which had $R_f$ values of 0.5 and 0.7 on TLC (AcOEt, silica gel) respectively. The desired monobromo product was purified by silica gel column chromatography eluted with AcOEt.

Ethyl N-(2-chloroacetamidoethyl) bromomalonamide (0.80 g, 0.0024 mol) was dissolved in 50 ml of absolute EtOH. To a stirred solution under N₂, a solution of potassium thiobenzoate (prepared from 0.155 g (0.004 mol) of potassium in 25 ml of absolute EtOH that was reacted with 0.57 g (0.004 mol) of thiobenzoic acid) was added. The reaction mixture was heated at 70°–75° C. for 3 hrs. After filtration while hot to remove precipitate the solvent was removed to yield 1.40 g of gummy residue. The residue was dried and then extracted several times with AcOEt. Material extracted was purified by passage through a silica gel column packed in CHCl₃ and eluted with AcOEt. The desired products, 0.75 g (63%) had an $R_f$ of 0.5 in AcOEt on silica gel TLC. Crystallization from EtOH gave an analytically pure sample, mp 143°–144° C.

EXAMPLE 2

Radiolabeling with Tc-99m

The following procedure is suitable for radio-labeling either the alcohol or carboxylate N₂S₂ ligand. Kits are prepared with the following amounts of components: 1.0 mg of N₂S₂ ligand, 20 mg of sodium glucoheptonate (other suitable exchange ligands may be gluconate, acetate, glycine, glucoheptonate, citrate, or glycolate), and 0.10 mg of stannous chloride dihydrate (or stannous fluoride) in lyophilized form or in about 1 ml volume of deoxygenated aqueous solution. When radiolabeling with Tc-99m is desired, the desired amount (mCi) of radioactivity is added in generator saline (up to 4 ml) and the resulting solution heated in a boiling water bath for 10 min. During that time an intermediate complex is first produced with the glucoheptonate or other labile ligand and the $N_2S_2$ ligand forms the desired final product by exchange. The purity of the final product is determined by HPLC using reversed phase conditions: 5 ODS, 4.6×250 mm column, ethanol/0.010M Pi (95:5), 1.0 ml/min flow rate. The hydroxy $N_2S_2$ complex gives two stereoisomeric peaks at 3.5 and 5.0 min.

1, 3-bis (mercaptoacetamido)-2-propanol (HO-DADS) of the following general formula:

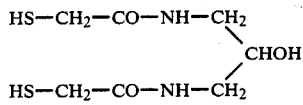

can be synthesized from the corresponding 1,3-diamino-2-propanol by the following sequences:

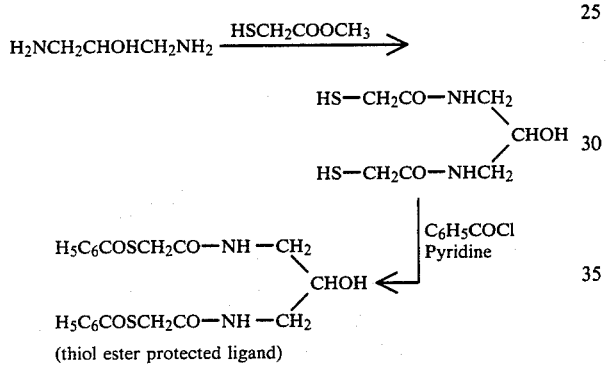

(thiol ester protected ligand)

Reaction of the diamino compound with methyl thioglycolate provides the bis thioacetamido derivative which is esterified with benzoyl chloride in pyridine to give the sulfhydryl protected ligand. The benzoyl groups are removed by mild base hydrolysis or metal assistance during chelation. More specifically, the 1,3-bis (mercaptoacetamido)-2-propanol may be made according to Example 3.

EXAMPLE 3

1,3-bis (mercaptoacetamido)-2-propanol 1, 3-Diamino-2-propanol (0.1 g, 0.011 mol) was dissolved in 10 ml of EtOH, and 2.76 g (0.026 mol) of methyl thioglycolate was added. The resulting solution was refluxed for 1 hour under $N_2$. After removal of solvent the residue was washed with 1:1 hexane/toluene to remove excess methylthioglycolate. The washed residue was dissolved in pyridine and 3 ml (3.62 g, 0.026 mol) of benzoyl chloride in 10 ml of pyridine was added dropwise while cooling in an ice bath. After addition was complete the mixture was added to water. The solid product (3.10 g, 68%) was isolated by filtration. Recrystallization from EtOH gave analytically pure material mp 175°–176° C.

The preparation of the corresponding Tc-99m complex follows the general procedure outlined in Example 2.

The carboxyl derivative 1,3-bis(mercaptoacetamido)-2-carboxy propane of the following general formula:

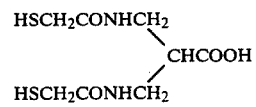

can be synthesized from the corresponding diamino compound by the following sequences:

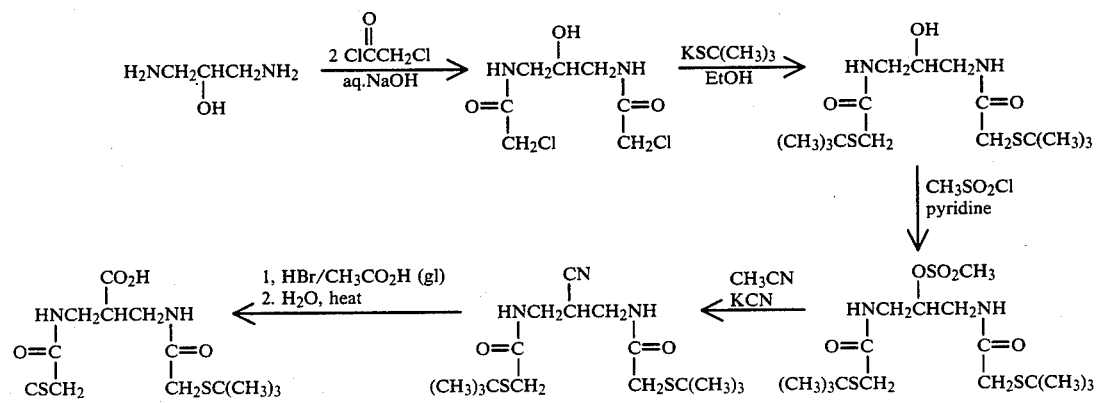

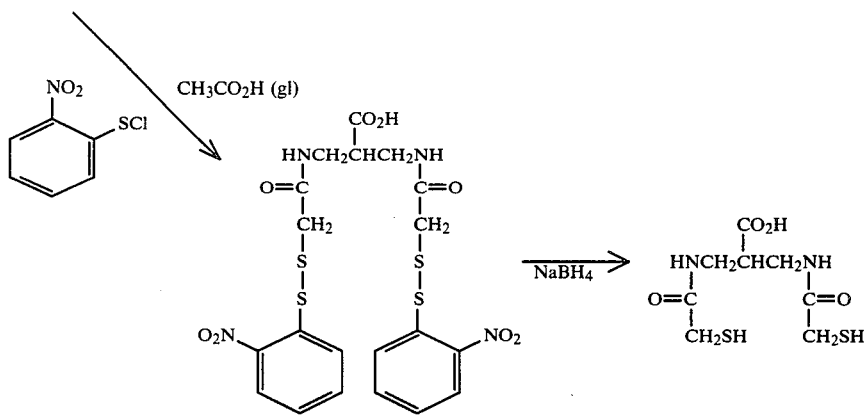

The diamino compound is acylated with chloroacetyl chloride, and sulfur is introduced with t-butyl thiolate. The hydroxyl group is then converted to the mesylate and then reacted with cyanide to give the additional carbon. The cyano group is subsequently hydrolyzed to the carboxylic acid, and the sulfur deprotected by reaction with o-nitrophenylsulfenyl chloride to give the disulfide. The disulfide is then reduced to the desired dithiol ligand with sodium borohydride.

A general method for the synthesis of N,N'-bis (benzoylmercaptoacetyl) diamines from starting diamino precursors is described as for ethyl D,L-N,N'-bis-(benzoylmercaptoacetyl)-2,4-diaminobutanoate in Example 4.

EXAMPLE 4

N,N'-bis(benzoylmercaptoacetyl)-2,4-diamino-butanoate

D,L-2,4-Diaminobutanoic acid-dihydrochloride (5.0 g, 0.026 mol) was dissolved in 300 ml of absolute ethanol. After bubbling HCL gas into the solution, the solution was refluxed for 12 hours. Removal of solvent left 5.70 g of the ester which was used without purification.

Ethyl D,L-2,4-diaminobutanoate (5.50 g, 0.025 mol) was combined with 200 ml of toluene and cooled in an ice bath. While stirring, 250 ml of saturated NaHCO$_3$ solution was added. Then 15.0 g (0.133 mol) of chloroacetyl chloride dissolved in 50 ml of toluene was added dropwise over a 1 hour period to the cooled, stirred mixture. During this period of time the additional solid NaHCO$_3$ was occasionally added to the reaction mixture. After completion of the addition, the reaction mixture was allowed to come to room temperature and stirring was continued for an additional 15 hours. The layers were separated and the aqueous layer was extracted several times with ethyl acetate. The extracts and toluene layer were combined, dried over Na$_2$SO$_4$, and solvent removed to give 7.0 g (93%) of product which was used without purification.

Ethyl D,L-N,N'-bis (chloroacetyl)-2,4-diaminobutanoate (5.0 g, 0.017 mol) was dissolved in 100 ml of absolute ethanol. To the stirred solution under nitrogen was added an ethanolic solution of potassium thiobenzoate (prepared from 1.30 g (0.0033 mol) of potassium in 25 ml of absolute ethanol to prepare potassium ethoxide which in turn was reacted with 4.60 g (0.033 mol) of thiobenzoic acid). The mixture was refluxed for 3 hours. The reaction mixtures was filtered while hot to remove precipitate and the filtrate concentrated under reduced pressure. The residue was dried and then washed with 50 ml of CHCl$_3$. The CHCl$_3$ suspension was filtered again and CHCl$_3$ removed to yield a light pink product. The product was purified by silica gel chromatography using CHCl$_3$ and AcOEt as successive eluting solvents. The final yield was 8.0 g (95%). Crystallization from ethanol was done for an elemental analysis sample: mp 141°–142° C.

The preparation of the corresponding Tc-99m complex follows the general procedure outlined in Example 2.

To prove the biological utility of the compounds according to the present invention, studies in both mice and humans were conducted.

Organ biodistribution studies were carried out in mice with groups sacrified at 10 min for comparative rates of renal excretion and 120 min for specificity determinations. I-131 hippuran was simultaneously administered as a reference comparison standard. The Tc-99m compounds were purified by HPLC and collected radioactivity diluted about 100-fold with saline before injection. About 1 uCi of the Tc-99m compound under study and 0.2 uCi of I-131 hippuran were injected via a tail vein in the mice.

The rates of renal excretion in humans were evaluated by the IV coadministration of about 10 uCi of the Tc-99m complex and 2 uCi of I-131 hippuran. Urine was collected at 30 min, 30–60 min, and 60–180 min post injection. The radioactivity in the urine was determined as a percentage of the administered dose for both the Tc-99m complex (individually determined for each HPLC component) and hippuran. The 30 min value provides an index of comparative rate of renal excretion and the 3 hour value indicates the specificity for renal excretion. The data collected for two of the compounds according to the present invention are contained in Table 1.

TABLE I

| Renal Excretion of Tc-99m Compounds in Humans | | | | | |
|---|---|---|---|---|---|
| Agent | 30 Min | (% OIH) | 60 Min | 180 Min | (% OIH) |
| Tc-99m HODADS-A | 49.4 | (81) | 64.6 | 78.5 | (85) |
| OIH | 60.7 | | 74.7 | 92.7 | |
| Tc-99m HODADS-B | 46.5 | (76) | 61.7 | 76.5 | (90) |
| OIH | 61.2 | | 74.0 | 84.5 | |
| Tc-αSCO$_2$DADS-A | 54.1 | (81) | 76.5 | 100.5 | (104) |
| OIH | 66.7 | | 80.7 | 97.0 | |
| Tc-αSCO$_2$DADS-B | 31.0 | (46) | 51.0 | 84.3 | (88) |

TABLE I-continued

Renal Excretion of Tc-99m Compounds in Humans

| Agent | 30 Min | (% OIH) | 60 Min | 180 Min | (% OIH) |
|---|---|---|---|---|---|
| OIH | 64.8 | | 78.8 | 95.4 | |

The data in Table 1 indicates that the Tc-99m HODADS appears promising in humans. Although the ligand results in stereoisomers in the middle chelate ring, both isomers in this case are excreted at similar rates (76 and 81% of hippuran at 30 min) and close to the 81% of OIH shown by Tc-$CO_2$DADS-A which has been shown in normal and patient studies to be a potentially useful Tc-99m radiopharmaceuticals (*J. Nucl. Med.* 25:40–48, 1984). In the case of Tc-99m HODADS, HPLC purification clearly would not be needed since both isomers are practically the same in humans. Thus the technological hurdle to commercial feasibility of Tc-99m $CO_2$DADS appears to be overcome.

The data in Table 1 also indicates that the Tc-99m-$\alpha SCO_2$DADS appears promising in humans. Peak A, containing 75% of the radioactivity present, was found at an average of 81% of hippuran at 30 min post injection. This is comparable to the desired A peak of Tc-99m $CO_2$DADS. The B component, containing 25% of the radioactivity, was found to the extent of 46% of hippuran at 30 min. Although indicated as slower than the A peak, B was moderately rapid, and a 3:1 mixture would be expected to be about 72% of hippuran, and thus usable without purification. By the end of 3 hours, 100% of A and 84% of B components were found in the urine. The lower value for component B probably reflects the slowness of the compound, and not a lack of specificity. Images of both A and B were of high quality.

The data obtained in mice for Tc-99m HODADS-A Table 2) and -B (Table 3) show that both HPLC components are excreted rapidly by the kidneys, A at 103% of I-131 hippuran and B at 95% of hippuran at 10 min post injection. Stomach values are low at all times indicating in vivo stability with respect to breakdown to give Tc-99m pertechnetate. Liver activity is evident, but does not appear to be intolerably high and decreases with time as shown by 120 min values. Intestinal activity is also seen, but at levels that may not result in imaging interference.

TABLE 2

BIODISTRIBUTION STUDY OF Tc-99m N,N′—BIS(MERCAPTOACETYL)-1-3-DIAMINO-2-HYDROXYPROPANE (HODADS), HPLC PEAK A IN MICE*

| | Blood | Liver | Kidneys | Stomach | Intestine | Urine |
|---|---|---|---|---|---|---|
| | \multicolumn{6}{c}{10 min post injection} | | | | | |
| Tc-99m | 4.04 | 3.12 | 5.01 | 0.28 | 5.40 | 70.21 |
| | ±0.27 | ±0.79 | ±1.01 | ±0.02 | ±0.54 | ±3.10 |
| I-131 | 4.08 | 1.49 | 3.62 | 0.52 | 1.03 | 68.09 |
| | ±0.37 | ±0.15 | ±0.99 | ±0.03 | ±0.09 | ±3.48 |
| | \multicolumn{6}{c}{120 min post injection} | | | | | |
| Tc-99m | 0.39 | 0.94 | 1.21 | 0.26 | 6.07 | 91.47 |
| | ±0.03 | ±0.07 | ±0.11 | ±0.07 | ±0.51 | ±1.05 |
| I-131 | 0.28 | 0.14 | 0.06 | 0.81 | 0.34 | 92.10 |
| | ±0.02 | ±0.01 | ±0.00 | ±0.13 | ±0.04 | ±1.30 |

*Data represent mean ± S.E.M. for 6 mice. Values for I-131 are those from simultaneously injected I-131 hippuran as a reference standard.

TABLE 3

BIODISTRIBUTION STUDY OF Tc-99m N,N′—BIS(MERCAPTOACETYL)-1-3-DIAMINO-2-HYDROXYPROPANE (HODADS), HPLC PEAK B IN MICE*

| | Blood | Liver | Kidneys | Stomach | Intestine | Urine |
|---|---|---|---|---|---|---|
| | \multicolumn{6}{c}{10 min post injection} | | | | | |
| Tc-99m | 3.81 | 7.97 | 5.72 | 0.32 | 8.19 | 61.47 |
| | ±0.24 | ±0.93 | ±0.54 | ±0.04 | ±0.82 | ±3.00 |
| I-131 | 4.22 | 2.29 | 2.27 | 0.61 | 1.37 | 64.98 |
| | ±0.31 | ±0.24 | ±0.21 | ±0.04 | ±0.10 | ±2.55 |
| | \multicolumn{6}{c}{120 min post injection} | | | | | |
| Tc-99m | 0.31 | 2.80 | 1.03 | 0.24 | 12.28 | 84.27 |
| | ±0.02 | ±0.07 | ±0.09 | ±0.05 | ±1.02 | ±0.98 |
| I-131 | 0.32 | 0.16 | 0.07 | 1.05 | 0.46 | 90.60 |
| | ±0.01 | ±0.00 | ±0.00 | ±0.17 | ±0.03 | ±0.66 |

*Data represent mean ± S.E.M. for 6 mice. Values for I-131 are those from simultaneously injected I-131 hippuran as a reference standard.

The data obtained in mice for Tc-99m$\alpha SCO_2$DADS-A (Table 4) and -B (Table 5) show that both HPLC components are excreted rapidly by the kidneys, although at 10 min post injection renal excretion is not as rapid as Tc-99m $CO_2$DADS-A, both A and B peaks of the complex are the same at 85% of hippuran. Stomach excretion is low indicating an in vivo stability of the complexes, and intestinal activity is slightly lower than hippuran. At 120 min post injection, virtually the only radioactivity of consequence is in the renal bladder indicating high specificity for renal excretion.

TABLE 4

Biodistribution Study of Tc-99m N—(Mercaptoacetyl)-N′(2-mercapto-3-oxopropanoate)-1,2-Diaminoethane, HPLC PEAK A IN MICE*

| | Blood | Liver | Kidneys | Stomach | Intes | Urine |
|---|---|---|---|---|---|---|
| | \multicolumn{6}{c}{10 min post injection} | | | | | |
| Tc-99m | 7.87 | 2.48 | 5.88 | 0.22 | 1.32 | 59.86 |
| | ±0.40 | ±0.24 | ±0.77 | ±0.01 | ±0.14 | ±3.80 |
| I-131 | 4.39 | 2.01 | 3.67 | 0.50 | 1.59 | 70.13 |
| | ±0.36 | ±0.20 | ±0.59 | ±0.05 | ±0.14 | ±3.94 |
| | \multicolumn{6}{c}{120 min post injection} | | | | | |
| Tc-99m | 0.12 | 0.05 | 0.28 | 0.01 | 0.21 | 97.60 |
| | ±0.07 | ±0.02 | ±0.11 | ±0.00 | ±0.02 | ±0.62 |
| I-131 | 0.26 | 0.17 | 0.27 | 1.11 | 0.39 | 96.05 |
| | ±0.04 | ±0.03 | ±0.10 | ±0.07 | ±0.01 | ±0.16 |

*Data represent mean ± S.E.M. for 3 mice. Values for I-131 are those from simultaneously injected I-131 hippuran as a reference standard.

TABLE 5

Biodistribution Study of Tc-99m N—(Mercaptoacetyl)-N′(2-mercapto-3-oxopropanoate)-1,2-Diaminoethane, HPLC PEAK B IN MICE*

| | Blood | Liver | Kidneys | Stomach | Intes | Urine |
|---|---|---|---|---|---|---|
| | \multicolumn{6}{c}{10 min post injection} | | | | | |
| Tc-99m | 7.54 | 3.82 | 5.68 | 0.21 | 1.31 | 57.40 |
| | ±0.39 | ±0.31 | ±0.41 | ±0.01 | ±0.09 | ±4.20 |
| I-131 | 4.42 | 2.20 | 2.91 | 0.58 | 1.52 | 67.26 |
| | ±0.33 | ±0.21 | ±0.19 | ±0.03 | ±0.13 | ±4.13 |
| | \multicolumn{6}{c}{120 min post injection} | | | | | |
| Tc-99m | 0.07 | 0.11 | 0.35 | 0.06 | 0.44 | 90.72 |
| | ±0.02 | ±0.02 | ±0.15 | ±0.02 | ±0.04 | ±1.42 |
| I-131 | 0.26 | 0.15 | 0.32 | 1.19 | 0.43 | 88.68 |
| | ±0.03 | ±0.01 | ±0.14 | ±0.12 | ±0.04 | ±1.35 |

*Data represent mean ± S.E.M. for 3 mice. Values for I-131 are those from simultaneously injected I-131 hippuran as a reference standard.

Thus, while I have illustrated and described the preferred embodiment of my invention, it is to be understood that this invention is capable of variation and modification, and I therefore do not wish to be limited to the precise terms set forth, but desire to avail myself of such changes and alterations which may be made for adapting the invention to various usages and conditions. Accordingly, such changes and alterations are properly intended to be within the full range of equivalents, and therefore within the purview, of the following claims.

Having thus described my invention and the manner and process of making and using it, in such full, clear, concise, and exact terms so as to enable any person skilled in the art to which it pertains, or with which it is most nearly connected, to make and use the same:

We claim:

1. A compound according to the formula:

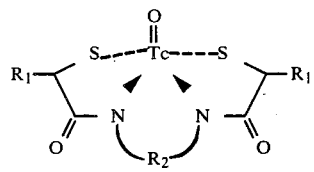

wherein $R_1$ is selected from the group —H, —$CH_2CH_3$, and —COOH; and wherein $R_2$ is selected from the group consisting of —$CH_2CH_2$—, and —$CH_2$—CH-R'—CHR"—; wherein R' and R" are selected from the group —H, —COOH, and —OH with the proviso R' and R", are not concurrently —H, and $R_1$ is not —H when $R_2$ is from the group —$CH_2CH_2$— and —$CH_2CH_2CH_2$—.

2. A compound according to claim 1 wherein $R_1$ is —COOH and $R_2$ is —$CH_2CH_2$—.

3. A compound according to claim 1 wherein $R_1$ is —COOH and $R_2$ is —$CH_2CHR'CHR''$.

* * * * *